United States Patent [19]

Rauleder et al.

[11] Patent Number: 5,068,382
[45] Date of Patent: Nov. 26, 1991

[54] PROCESS FOR THE PRODUCTION OF ORGANOSILICON COMPOUNDS

[75] Inventors: Hartwig Rauleder; Hans-Joachim Kötzch, both of Rheinfelden, Fed. Rep. of Germany

[73] Assignee: Huels Aktiengesellschaft, Marl, Fed. Rep. of Germany

[21] Appl. No.: 491,775

[22] Filed: Mar. 12, 1990

[30] Foreign Application Priority Data

Mar. 17, 1989 [DE] Fed. Rep. of Germany ....... 3908791

[51] Int. Cl.$^5$ .............................. C07F 7/08; C07F 7/18
[52] U.S. Cl. ................................................... 556/495
[58] Field of Search ........................................ 556/445

[56] References Cited

U.S. PATENT DOCUMENTS

| | | | |
|---|---|---|---|
| 3,658,866 | 4/1972 | Tsuji ............................... | 556/445 X |
| 3,681,418 | 8/1972 | Pierce et al. ..................... | 556/445 X |
| 3,957,843 | 5/1976 | Bennett ............................ | 556/445 X |
| 4,814,409 | 3/1989 | Blevins et al. ................... | 556/445 X |

*Primary Examiner*—Paul F. Shaver
*Attorney, Agent, or Firm*—Felfe & Lynch

[57] ABSTRACT

Organosilicon compounds of the formula

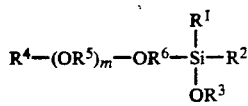

wherein
$R^1$ and $R^2$ are each independently straight or branched alkyl of 1 to 4 carbon atoms or —$OR^3$,
$R^3$ is $R^4$—$(OR^5)_m$—,
$R^6$ is straight or branched alkyl of 1 to 4 carbon atoms,
m is an integer from 0 to 6, inclusive,
$R^5$ is straight or branched alkylene of 2 to 4 carbon atoms, which may be identical or different when m is an integer from 2 to 6, and $R^6$ is straight or branched alkylene of 2 to 6 carbon atoms, are prepared by reacting hydrogensilanes of the formula

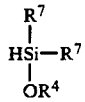

wherein
$R^7$ are identical or different groups $R^4$ or the group $OR^4$, and $R^4$ has the previously indicated meaning,
with terminally unsaturated ethers of the formula

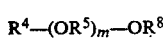

wherein
m, $R^4$ and $R^5$ have the previously indicated meanings, and
$R^8$ is terminally unsaturated straight or branched alkenyl or 2 to 6 carbon atoms,
in the presence of a catalyst at controlled temperatures to form addition products of the formula

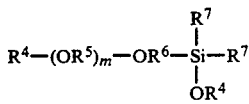

wherein
m and $R^4$, $R^5$, $R^6$ and $R^7$ have the previously indicated meanings, and the $R^4$'s are identical or different
which are converted into the desired end products by thermal and/or catalytic transesterification with monofunctional hydroxy compounds of the formula

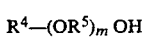

wherein
m, $R^4$ and $R^5$ have the previously indicated meanings.

8 Claims, No Drawings

PROCESS FOR THE PRODUCTION OF ORGANOSILICON COMPOUNDS

FIELD OF THE INVENTION

The subject matter of this invention is a novel process for the production of compounds of the formula

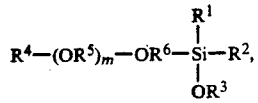 (I)

wherein
R$^1$ and R$^2$ are each independently straight or branched alkyl of 1 to 4 carbon atoms or —OR$^3$,
R$^3$ is R$^4$—(OR$^5$)$_m$—,
R$^4$ is straight or branched alkyl of 1 to 4 carbon atoms,
m is an integer from 0 to 6, inclusive,
R$^5$ is straight or branched alkylene of 2 to 4 carbon atoms, which may be identical or different when m is an integer from 2 to 6, and
R$^6$ is straight or branched alkylene of 2 to 6 carbon atoms.

BACKGROUND OF THE INVENTION

These substances are known as constituents of hydraulic fluids according to German Patent 26 52 719. The hydraulic fluids described there have, in spite of their superior hydraulic properties, not yet been used on an industrial scale. The production route of the German patent by reaction of chloroalkylsilane esters with alcoholates has deficiencies and leads to incomplete reaction. Resin formation, low purity and high chlorine content, as a source of corrosion in the hydraulic system, prevent their use.

OBJECTS OF THE INVENTION

Therefore there existed the object of producing the substances of the formula I by a superior procedure and on a technical scale, and in particular of making these substances available in satisfactory quality for use as components of hydraulic fluids.

DESCRIPTION OF THE INVENTION

The solution of this object consists in a new procedure. We have found that, by catalytic addition of hydrogensilanes of the formula

 (II)

wherein
R$^7$ are identical or different groups R$^4$ or the group OR$^4$, and R$^4$ has the previously indicated meaning, to terminally unsaturated ethers of the formula

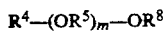 (III)

wherein
m, R$^4$ and R$^5$ have the previously indicated meanings, and
R$^8$ is terminally unsaturated straight or branched alkenyl of 2 to 6 carbon atoms, addition products of the formula

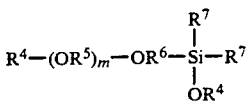 (IV)

wherein
m and R$^4$, R$^5$, R$^6$, and R$^7$ have the previously indicated meanings, and the R$^4$'s are identical or different, are formed with high yield and purity, provided, however, that a defined temperature control is maintained. The products of the formula (IV) can be converted into compounds of the formula (I) by thermal and/or catalytic transesterification with monofunctional hydroxy compounds of the formula

 (V)

wherein
m, R$^4$ and R$^5$ have the previously indicated meanings.

This transesterification is important if a radical —R$^3$ with a long-chain, that is, with at least one or several glycol groups, is to be introduced by means of the monofunctional hydroxy compound.

The principle of the catalytic addition of hydrogenalkoxysilanes or hydrogenalkylalkoxy silanes is known as such, but the known procedure leads to impure products with poor yields. We have found that the substances of the formula (III) with the terminally unsaturated structure isomerize in the exothermic addition reaction, with the double bond being displaced and the isomer no longer being susceptible to addition to hydrogensilanes. Substance losses occur as a result of this. However, particularly poisoning of the catalyst takes place, and further additions of the catalyst are ineffective.

We have found that by controlling the temperature so that it does not exceed 130° C., preferably 110° C. at the most, the catalyst remains active, small amounts of catalyst are needed, and high yields of the product IV as well as a lower isomerization are achievable.

The transesterification of the product of the formula (IV) with hydroxy compounds of the formula (V) are not known. We have found that the product IV, in contrast to the substance V, possesses a significant stability, especially if two or three radicals-R$^3$ are to be introduced.

We have found that a quantitative transesterification and very pure products are achievable, especially if the compound V is used in excess and/or titanium esters or zirconium esters are used as catalysts for acceleration of the reaction, with the simultaneous possibility of lowering the reaction temperature.

The process can be carried out continuously or discontinuously.

Compounds II and III can be brought to reaction in admixture with one another or in admixture with the catalyst. The catalyst is used especially in amounts of 10$^{-2}$ to 10$^{-8}$ mol per mol of product. The control of the reaction and the temperature regulation can take place by means of a thermostat. Temperature ranges between 25° and 130° C., preferably between 35° and 110° C. are to be maintained. Temperature regulation is also possible by means of the excess of one component. Excesses of one component in the molar ratio up to 1:8 can be used. Even the use of solvents in ratios up to 1:8 is possible. The solvents must be inert in the reaction.

The isolation of the product of the formula (IV) takes place by distillation, preferably at reduced pressure. A lower limit for the reduced pressure cannot be indicated. In general, however, compounds of the formula (IV) and of the formula (I) can be separated from the starting compounds and the impurities at <10 mbar. Insofar as the substances IV are reacted with the substances V to form substances I, temperatures of 90° to 240° C. are possible as reaction temperature. It is possible to operate with and without a catalyst.

Suitable hydrogensilanes of the formula (II) are hydrogen trialkoxysilanes as well as hydrogen monoalkyldialkoxy silanes or hydrogen dialkylmonoalkoxy silanes wherein the alkyl group and the alkoxy group contain 1 to 4 carbon atoms independent of one another. Examples are trimethoxysilane, methyldimethoxysilane, ethyldimethoxysilane dimethylmonomethoxysilane, methylisobutylmonomethoxysilane, triethoxysilane, methyldiethoxysilane, propyldiethoxysilane, tri-sec.-butoxysilane and methyldiisobutoxysilane.

Starting materials of the formula (III) are, for example, the following glycol- or polyglycol-alkyl-alkenyl ethers: ethyleneglycol-n-butyl-butene-1-yl-4-ether, propyleneglycol-2-methyl-2-methallyl ether, 1-methoxy-4-vinyloxybutane, propyl-vinyl ether and propyl-methallyl ether, diethyleneglycol-monomethyl-pentene-1-yl-5-ether, diethyleneglycol-monomethyl-monoallyl ether, triethyleneglycol-monomethyl-monoallyl ether, triethyleneglycol-monoethyl-monomethallyl ether, triethyleneglycol-monobutyl-monoallyl ether, methyltetraglycolallyl ether, butyltetraglycolallyl ether, ethyltetraglycolvinyl ether, and methylpentaglycolallyl ether.

In the foregoing, tetraethyleneglycol for example means the ether of 4 molecules of ethyleneglycol. The ethers of, for example, two molecules of ethyleneglycol or six molecules of ethyleneglycol are also called diglycol and hexaglycol, respectively.

The ether (III) with terminally unsaturated alkenyl groups can be produced by following the Williamson Synthesis by conversion of hydroxy compounds V into the alkali metal alcoholate and subsequent reaction with alkenyl halides of 2 to 6 carbon atoms.

Catalysts are preferably used in the production of the compounds of the formula (IV), that is, the hydrolysis of the alkenyl ethers. Suitable catalysts in the production of the addition products IV are salts or complex salts of elements of the eighth sub-group of the Periodic System, especially of nickel, ruthenium, rhodium, palladium or, very preferbly, platinum. Solutions in, for example, acetone, mesityl oxide, isopropanol or acetoacetic esters are convenient. Suitable catalysts are, in particular, hexachloroplatinic acids, salts of nickel, ruthenium, rhodium or palladium. Preferred are acetylacetonates as well as acetates.

Of importance is the presence of the catalyst metals in soluble form as cation or complex. The temperature regulation to no more than 130° C. can be controlled by addition of solvents, in particular hydrocarbons like hexane, heptane or toluene, and by an excess or the slow addition of one or both reaction components.

The compounds of the formula (IV) which are produced are, for example, $CH_3(OC_2H_4)_5O(CH_2)_3Si(OCH_3)_3$, $CH_3(OC_2H_4)_4O(CH_2)_2Si(OCH_3)_3$, $n-C_4H_9(OC_2H_4)_4O(CH_2)_3Si(OCH_3)_3$, $n-C_4H_9(OC_2H_4)_3O(CH_2)_3Si(OC_2H_5)_3$, $C_2H_5(OC_2H_4)_3OCH_2CH(CH_3)CH_2Si(OC_2H_5)_3$, $CH_3(OC_2H_4)_3O(CH_2)_3Si(CH_3)(OCH_3)_2$, $CH_3(OC_2H_4)_3O(CH_2)_3Si(OC_2H_5)_3$, $CH_3(OC_2H_4)_3O(CH_2)_2Si(OCH_3)_3$, $CH_3(OC_2H_4)_3O(CH_2)_3Si(OCH_3)_3$, $CH_3(OC_2H_4)_2O(CH_2)_3Si(OC_2H_5)_3$, $CH_3OC_2CH(CH_3)OCH_2CH(CH_3)CH_2Si(OC_2H_5)_3$, $CH_3OCH_2CH(CH_3)OCH_2CH(CH_3)CH_2Si(CH_3)(O-sec-C_4H_9)_2$, $CH_3(OC_2H_4)_3O(CH_2)_5Si(OCH_3)_3$.

Preferably, at least one group —OR⁵— of the alkyleneglycol is contained in these products.

Insofar as one or several residues —OR³ are to be bound to Si in the compounds of the formula (I), the distillation of the compounds IV is followed by the transesterifidation with hydroxy compounds of the formula (V), which preferably contain a glycol group or a polyglycol ether group —OR⁵—. Siutable glycolmonoethers of the formula (V) are, for example, methyldiglycol, methyltriglycol, ethyltriglycol, butyltriglycol, methyltetraglycol, butyltetraglycol, methylpentaglycol, 1-methylpropanol-2, and 4-propoxybutanol-1.

End products of the process can be the substances of the formula (I) or the substances of the formula (IV). The substances of the formula (I) are formed from substances of the formula (IV) by transesterification with substances of the formula (V), whereby the groups —OR⁴ in the substances of the formula (IV) are replaced by the groups —OR³ in the substances of formula (I).

Preferably, transesterification catalysts are used, although the transesterification can also be carried out without catalysts at elevated temperatures. Suitable transesterification catalysts are titanium orthdosters and zirconium orthometers, that is, orthoalkyltitanates or orthoalkylzirconates wherein the alkyl group contains preferably 1 to 4 carbon atoms.

n-, iso or sec.butylorthotitanate or zirconate are preferred. Also suitable are the corresponding oligomeric titanates or zirconates which are produced from the orthoesters by partial hydrolysis. The amount of the catalyst is less than 0.1% by weight, based on the amount of substance I.

Examples of the organosilicon compounds of the formula (I) are:

$CH_3(OC_2H_4)_5O(CH_2)_3Si[(OC_2H_4)_3OCH_3]_3$, $CH_3(OC_2H_4)_4O(CH_2)_3Si[(OC_2H_4)_3OCH_3]_3$, $n-C_4H_9(OC_2H_4)_4O(CH_2)_3Si[(OC_2H_4)_3OCH_3]_3$, $n-C_4H_9(OC_2H_4)_3O(CH_2)_3Si[(OC_2H_4)_3OCH_3]_3$, $C_2H_5(OC_2H_4)_3OCH_2CH(CH_3)CH_2Si[(OC_2H_4)_3OC_2H_5]_3$, $C_2H_5(OC_2H_4)_3O(CH_2)_3Si[(OC_2H_4)_3OCH_3]_3$, $C_2H_5(OC_2H_4)_3O(CH_2)_2Si[(OC_2H_4)_3OCH_3]_3$, $CH_3(OC_2H_4)_3O(CH_2)_3Si(CH_3)[(OC_2H_4)_3OCH_3]_2$, $CH_3(OC_2H_4)_3O(CH_2)_3Si[(OC_2H_4)_3OCH_3]_3$, $CH_3(OC_2H_4)_3O(CH_2)_3Si[(OC_2H_4)_3OC_2H_5]_3$, $CH_3(OC_2H_4)_3O(CH_2)_3Si[(OC_2H_4)_3OC_4H_9]_3$, $CH_3(OC_2H_4)_3O(CH_2)_3Si[(OC_2H_4)_3OCH_3]_3$, $CH_3(OC_2H_4)_2O(CH_2)_3Si[(OC_2H_4)_3OCH_3]_3$, $CH_3OCH_2CH(CH_3)OCH_2CH(CH_3)CH_2Si[OCH(CH_3)CH_2OCH_3]_3$, and $CH_3(OC_2H_4)_3O(CH_2)_5Si[(OC_2H_4)_3CH_3]_3$.

In the organosilicon compounds a group $-OR^5-$ is preferably connected to the residue $-OR^6$ of formula (I). Polyglycol residues, that is, diglycol residues up to pentaglycol residues, that is, residues of polyethers, especially of ethyleneglycol, are preferred as the residue $OR^5$. It is very much preferred that the substances of the formula (I) contain three residues $OR^3$ with at least one glycol residue, which are preferably the same.

The following examples illustrate the present invention and will enable others skilled in the art to understand it more completely. It should be understood, however, that the invention is not limited solely to the particular examples given below.

EXAMPLE 1

$CH_3(OC_2H_4)_3O(CH_2)_3Si[(OC_2H_4)_3]_3$

A) Production of the trimethyl ester 489 g of trimethoxy silane (4 mols) together with 153 g (0.75 mol) of triethyleneglycol-monomethyl-monoallyl ether and 0.5 ml of a solution with 1% by weight $H_2PtCl_6.6H_2O$ in acetone were heated to 52° C. in a 2-liter flask equipped with a thermostatically controlled heater, internal thermometer, stirrer, measuring funnel and $N_2$-blanketed reflux condenser. After 20 minutes, the reaction started. Within 1 minute the internal temperature increased to 83° C. and fell within 9 minutes, regulated by the thermostat temperature, to 67° C. Then, a further 856 g (4.10 mols) of triethyleneglycol-monomethylmonoallyl ether were added within 95 minutes at a rate of 9 g/min while holding the thermostat temperature at 52° C., with a reaction temperature being set between 66° and 74° C. After the end of the addition, the reaction mixture was still stirred at 61° C. for 80 minutes and then was worked up by vacuum distillation. 1.298 g of 3-methyltri.lgycol-oxypropylsilane-trimethyl ester were isolated. Yield: 99.4%, based on trimethoxy silane, and 80.5% based on triethyleneglycol-monomethyl-monoallyl ether. 190 g of triethyleneglycol-monomethylmonopropenyl ether were isolated as by-product.

B.p. 144° C. (2 mbar).
$D.4^{20}$ 1.049;
$n_D$ 1.4328;

Viscosity (20° C.) 5.93 mPa.s;

B) Production of the tris-methyltriglycol ester

In an apparatus according to A), the reflux condenser was exchanged for a vacuum distillation arrangement, and a mixture of 326.5 g (1 mol) of 3-methyltriglycoloxypropyl silane-trimethyl ester and 657 g (4 mols) of methyltriglycol was introduced. 84 g of methanol were distilled off within 8 hours at 200 mbar at an internal temperature of 180° C. increasing to 226° C. and then, as the vacuum dropped, a further 12 g of methanol were trapped in the cooling trap, and 164 g of methyltriglycol were distilled off. 715 g of 3-methyltriglycol-oxypropyl silane-tris-methyltriglycol ester, corresponding to a 99% yield, remained in the reactor.

$D.4^{20}$ 1.087 ($D.4^{20}$=normal density at 20° C., measured against the density of water at 4° C.).
$n_D^{20}$ 1.4538 ($n_D^{20}$=the refractive index at 20° C.).
Viscosity (20° C.) 27.8 mPa.s.

EXAMPLE 2

$CH_3(OC_2H_4)_3O(CH_2)_3Si[(OC_2H_4)_3OCH_3]_3$

Example 1B) was repeated, but 0.5 ml of tetrabutyltitanate was added to the reaction mixture. As a result, the transesterification reaction commenced already at 115° C. After 3 hours at 120° C., the reaction mixture was heated for 1 hour at 139° C. After distilling off the excess methyltriglycol (164 g) in vacuo, 719 g of product were obtained.

EXAMPLE 3

$CH_3(OC_2H_4)_3O(CH_2)_3Si[(OC_2H_4)_3OCH_3]_3$ from the triethyl ester

In the same way as in Example 1A), 982 g (4.54 mols) of triethyleneglycol-monomethyl-monoallyl ether together with 164 g (1 mol) triethoxy silane and 0.5 ml of the catalyst solution of Example 1 were heated to 48° C. The reaction commenced after 35 minutes and the temperature immediately rose to 78° C. After cooling to 62° C., a further 164 g (1 mol) of triethoxy silane were added, whereupon the temperature increased to 86° C. Next, at 63° C., again 164 g of triethoxy silane were added with increase in temperature to 82° C. Then, at 66° C., a further 164 g of triethoxy silane were added with subsequent temperature increase to 79° C. The temperature fell to 59° C. in 80 minutes. Then, 1.456 g of 3-methyltriglycoloxpropylsilane-triethyl ester were isolated by distillative working up (yield: 88% based on triethyleneglycol-monomethyl-monoallyl ether, and 99% based on triethoxy silane.

B.p. 154° C. (2 mbar);
$D.4^{20}$ 0.999;
$n_D^{20}$ 1.4305;
Viscosity (20° C.) 5.18 mPa.s.

The transesterification with methyltriglycol was carried out in the same way as in Example 2 with 1 mol of the produced triethyl ester and yielded 720 g of pure end product.

EXAMPLE 4

$CH_3(OC_2H_4)_3OCH_2CH(CH_3)CH_2Si[(OC_2H_4)_3OCH_3]_3$ from the trimethyl ester In the same way as in Example 3, 959 g (4.4 mols) of triethyleneglycol-monomethyl-monomethallyl ether were reacted four times with 122 g (1 mol) of trimethoxy silane. The distillative working up yielded 1.240 g of trimethyl ester (91%: yield based on methallyl ether; 98% based on trimethoxy silane).

B.p. 142° C. (1 mbar);
$D_4^{20}$ 1.033;
$n_D^{20}$ 1.4333;
Viscosity (20° C.) 6.22 mPa.s.

The transesterification reaction with methyltriglycol was carried out with 1 mol of trimethyl ester in the same way as in Example 2 and yielded 730 g of pure end product.

$D_4^{20}$ 1.079;
$n_D^{20}$ 1.4527;
Viscosity (20° C.) 28.8 mPa.s.

EXAMPLE 5

$CH_3(OC_2H_4)_3OCH_2CHCH(CH_3)CH_2Si[(OC_2H_4)_3OCH_3]_3$ from the triethyl ester In the same way as in Example 1, 657 g (4 mols) of triethoxysilane were reacted with 176 g (0.8 mol) of triethyleneglycol-monomethyl-monomethallyl ether, the internal temperature increasing initially to 87° C. Then, in the same way as in Example 1 a further 762 g (3.5 mols) of methallyl ether were added at a rate of about 10 g per minute. The working up yielded 1.505 g of triethyl ester (98% yield based on triethoxy silane).

B.p. 146° C. (1 mbar);
$D_4^{20}$ 0.991;
$n_D^{20}$ 1.4309;
Viscosity (20° C.) 5.42 mPa.s.

The transesterification with methyltriglycol was carried out with 1 mol of triethyl ester in the same way as in Example 2 and yielded 730 g of pure end product.

EXAMPLE 6

$CH_3(OC_2H_4)_3O(CH_2)_3Si(CH_3)[(OC_2H_4)_3OCH_3]_2$ from methyl hydrogen dimethoxysilane In the same way as in Example 3, 878 g (4.3 mols) of triethyleneglycol-monomethyl-monoallyl ether were heated together with 106 g (1 mol) of methyl hydrogen dimethoxysilane and 0.4 ml of catalyst solution to 45° C. After 15 minutes, the reaction commenced and the temperature rose immediately to 81° C. and fell within 12 minutes, regulated by the thermostat temperature, again to 58° C. Then, a further 319 g (3 mols) of methyl hydrogen dimethoxysilane were metered in within 80 minutes at a rate of about 4 g per minute while maintaining a thermostat temperature of 49° C., with a reaction temperature being set between 59° C. and 63° C. There was further stirring for 120 minutes at 61° C. and then working up by vacuum distillation. 1.223 g of Si-methyl-3-methyltriglycoloxypropyl-dimethoxy silane were isolated. The yields were 98.5% based on the methyl hydrogen dimethoxy silane and 93° C. based on the methyltriglycolallyl ether. 60 g of methyltriglycolpropenyl ether were isolated as by-product.

B.p. 135° C. (1 mbar);
$D_4^{20}$ 1.014;
$n_D^{20}$ 1.4359;
Viscosity (20° C.) 6.13 mPa.s.

In the same way as in Example 1B), 310.5 g (1 mol) of the foregoing silane were transesterified with 657 g (4 mols) methyltriglycol at 160° to 196° C. After distillative separation of about 63 g of methanol and 327 g of methyltriglycol, 561 g of Si-methyl-3-methyltriglycoloxypropylsilane-bis-methyltriglycol ester, corresponding to a 98% yield, were obtained.

$D_4^{20}$ 1.063;
$n_D^{20}$ 1.4524;
Viscosity (20° C.) 21.6 mPa.s.

EXAMPLE 7

$CH_3OCH_2CH(CH_3)OCH_2CH(CH_2Si[OCH(CH_3)CH_2OCH_3]_3$ from the triethyl ester 577 g (4 mols) of 1-methoxypropyl-2-methallyl ether were heated to 54° C. in an apparatus according to Example 1A), 0.4 ml of catalyst were added in the same way as in Example 1, and the mixture was reacted exothermically in about 170 minutes by metering in 657 g (4 mols) of triethoxy silane at the rate of about 4 g per minute. An average reaction temperature of about 88° C. (thermostat temperature 54° C.) was set for this. After the end of the addition, the reaction temperature dropped within about 45 minutes to 54° C. Then 1.280 g of 3-(1'-methoxy-2'-propoxy)-2-methylpropylsilanetriethyl ester (about 96% yield) were isolated by distilative working up.

B.p. 103° C. (1 mbar);
$D_4^{20}$ 0.942;
$n_D^{20}$ 1.4182;
Viscosity (20° C.) 2.23 mPa.s.

317 g (1 mols) of the foregoing triethyl ester were refluxed in a 12-plate packed column with automatic column head for 38 hours with 630 g (7 mols) 1-methoxy-propanol-2 and 0.3 ml of tetraethoxytitanium with slow distillative removal of a total of 272 g of ethanol and 90 g of 1-methoxypropanol (at the end in vacuo at about 50 mbar and 210° C.). 862 g (about 98% yield) were obtained by means of final rectification in vacuo.

B.p. 141° C. (1 mbar);
$D_4^{20}$ 0.986;
$n_D^{20}$ 1.4306;
Viscosity (20° C.) 7.89 mPa.s.
Viscosity (−40° C.) 248 mPa.s;
Flash point: 130° C.

EXAMPLE 8

$CH_3OCH_2CH_2OCH_2CH_2O(CH_2)_3Si[(OCH_2CH_2)_2OCH_3]_3$ from triethoxy silane 657 g (4 mols) triethoxy silane and 120 g (0.75 mol) of methyldiglycolallyl ether were reacted in the same way as in Example 1A), and then reacted at 69° C. in 75 minutes with a further 567 g (3.54 mols) of methyldiglycolallyl ether (8 g per minute). the distillative working up yielded 1.272 g of methyldiglycoloxypropylsilane-triethyl ester (98% yield, based on triethoxy silane).

B.p. 125° C. (1 mbar);
$D_4^{20}$ 0.984;
$n_D^{20}$ 1.4246;
Viscosity (20° C.) 3.67 mPa.s.

The transesterification of 1 mol with methyldiglycol in the presence of 0.4 ml zirconium tetrapropylate in the same way as in Example 2 yielded 537 g of product (yield: 98%).

$D_4^{20}$ 1.077;
$n_D^{20}$ 1.4480;
Viscosity (20° C.) 15.6 mPa.s.

EXAMPLE 9

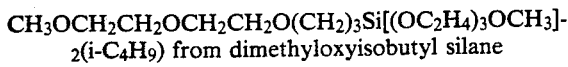
from dimethyloxyisobutyl silane

In the same way as in Example 3, 692 g (4.32 mols) of diethyleneglycol-monomethyl-monoallyl ether were heated to 58° C. with 148 g (1 mol) of isobutyl hydrogen dimethoxy-silane and 0.4 g of the catalyst solution. After 12 minutes, the temperature increased to 89° C. After lowering the temperature to 72° C., a further 445 g (3 mols) of isobutyl hydrogen dimethoxy-silane were metered in (5 g per minute) at a temperature of 73° C. within 90 minutes. Further stirring took place at 58° C. for 300 minutes. the distillative working up yielded 1.185 g of Si-isobutyl-3-methyl-diglycoloxypropyl-dimethoxy-silane (96% yield, based on the hydrogensilane).

B.p. 121° C. (1 mbar);
$D_4^{20}$ 0.981;
$n_D^{20}$ 1.4230;
Viscosity (20° C.) 3.32 mPa.s.

The transesterification of 1 mol with methyltriglycol in the presence of 0.2 ml tetrapropyl titanate in the same way as in Example 2 yielded 557 g of product (yield: 97%).

$D_4^{20}$ 1.052;
$n_D^{20}$ 1.4498;
Viscosity (20° C.) 20.7 mPa.s.

EXAMPLE 10

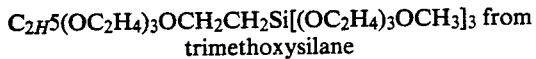
from trimethoxysilane

The reaction with 153 g (0.75 mol) triethyleneglycol-monoethyl-monovinyl ether and 489 g (4 mols) of trimethoxysilan was started at 78° C., in the same way as in Example 1. The temperature increased to 84° C. A further 564 g (3.25 mols) of ethyltriglycol-vinyl ether (3 g per minute) were metered in over 180 minutes. Further stirring took place at 92° C. for 180 minutes. The distillative working up yielded 1.282 g of 2-ethyltriglycoloxyethylsilane-trimethyl ester (98% yield).

B.p. 143° C. (2 mbar);
$D_4^{20}$ 1.050;
$n_D^{20}$ 1.4326;
Viscosity (20° C.) 5.90 mPa.s.

The transesterification into the tris-methyltriglycol ester took place in the same way as in Example 2.
$D_4^{20}$ 1.088;
$n_D^{20}$ 1.4538;
Viscosity (20° C.) 27.7 mPa.s.

EXAMPLE 11

$C_2H_5(OC_2H_4)_3O(CH_2)_3Si(OR^3)_3.OR^3$ ($OR^3$=methoxy, -ethoxy-, -methyltriglycol-, -ethyltriglycol-, -butyl-triglycol residue) from trimathoxysilane In the same way as in Example 1, 164 g (0175 mol) of triethyleneglycol-monoethyl-monoallyl ether were reacted at 52° C. with 489 g (4 mols) of trimethoxysilane, and the reaction was completed with a further 864 g (3.96 mols) of triethyleneglycol-monoethyl-monoallyl ether. The distillative working up yielded 1.338 g of 3-ethyltriglycoloxypropylsilane-trimethvl ester (96% yield, based on trimethoxysilane).

B.p. 145° C. (1 mbar);
$D_4^{20}$ 1.031;
$n_D^{20}$ 1.4322;
Viscosity (20° C.) 6.32 mPa.s.

Triethyl ester, produced in the same way as in Example 3. Yield: 99%, based on triethoxysilane, and 89% based on triethyleneglycol-monoethyl-monoallyl ether.

B.p. 155° C. (1 mbar);
$D_4^{20}$ 0.989;
$n_D^{20}$ 1.4302;
Viscosity (20° C.) 5.49 mPa.s.

Tris-methyltriglycol ester, produced from the trimethylester with methyltriglycol, in the same way as in Example 2.

$D_4^{20}$ 1.080;
$n_D^{20}$ 1.4538;
Viscosity (20° C.) 29.8 mPa.s.

Tris-ethyltriglycol ester, produced from the triethylester with ethyltriglycol in the same way as in Example 2.

$D_4^{20}$ 1.076;
$n_D^{20}$ 1.4537;
Viscosity (20° C.) 39.2 mPa.s.

Tris-butyltriglycol ester, produced from the trimethylester with butyltriglycol in the same way as in Example 2.

$D_4^{20}$ 1.072;
$n_D^{20}$ 1.4540;
Viscosity (20° C.) 40.6 mPa.s.

EXAMPLE 12

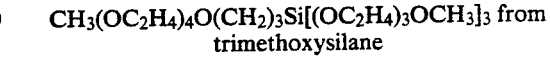
from trimethoxysilane 186 g (0.75 mol) of tetraethyleneglycol-monomethyl-monoallyl ether were reacted with 4 mols of trimethoxysilane at 52° C. starting temperature, in the same way as in Example 1, and the reaction was completed with a further 973 g (3.92 mols) tetraethyleneglycol-monomethyl-monoallyl ether. 1.450 g of 3-methyl-tetraglycoloxypropyl-trimethoxysilane were isolated. Yield: 98%, based on trimethoxysilane.

B.p. 168° C. (1 mbar);
$D_4^{20}$ 1.057;
$n_D^{20}$ 1.4372;
Viscosity (20° C.) 8.65 mPa.s.

Tris-methyltriglycol ester, produced in the same way as in Example 2:
$D_4^{20}$ 1.084;
$n_D^{20}$ 1.4537;
Viscosity (20° C.) 32 mPa.s.

EXAMPLE 13

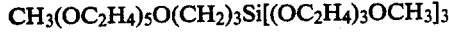

73 g (0.25 mol) of pentaethyleneglycol-monomethyl-monoallyl ether were reacted with 1 mol of trimethoxysilane at 52° C. starting temperature in the same way as in Example 1, and the reaction was completed with a further 251 g (0.86 mol) of pentaethyleneglycol-monoethyl-monoallyl ether at 82° C. 402 g of 3-methyl-pentaethyleneglycoloxypropyl-trimethoxysilane (97% yield, based on the hydrogensilane) were isolated.

B.p. 184° C. (1 mbar);
$D_4^{20}$ 1.064;
$n_D^{20}$ 1.4421;
Viscosity (20° C.) 12.4 mPa.s.

Tris-methyltriglycol ester, produced from the trimethylester in the same way as in Example 2:
$D_4^{20}$ 1.086;
$n_D^{20}$ 1.4549;

Viscosity (20° C.) 39.2 mPa.s.

EXAMPLE 14

$C_4H_9(OC_2H_4)_4O(CH_2)_3Si[(OC_2H_4)_3OCH_3]_3$ 73 g (0.25 mol) of tetraethyleneglycol-monobutyl-monoallyl ether were reacted with 1 mol of trimethoxysilane at 52° C. starting temperature in the same way as in Example 1, and the reaction was completed with a further 256 g (0.88 mol) of tetraethyleneglycol-monobutyl-monoallyl ether. 392 g of 3-butyltriglycoloxypropyl-trimethoxysilane (95% yield, based on the hydrogensilane) were isolated.

B.p. 180° C. (1 mbar);
$D_4^{20}$ 1.023;
$n_D^{20}$ 1.4381;
Viscosity (20° C.) 10.2 mPa.s.

Tris-methyltriglycol ester, produced from the trimethylester in the same way as in Example 2:
$D_4^{20}$ 1.070;
$n_D^{20}$ 1.4545;
Viscosity (20° C.) 37.0 mPa.s.

EXAMPLE 15

$CH_4H_4(OC_2H_4)_3O(CH_2)_3Si[(OC_2H_4)_3OCH_3]_3$ 172 g (0.7 mol) of triethyleneglycol-monobutyl-monoallyl ether were reacted at 52° C. starting temperature with 3 mols of triethoxysilane in the same way as in Example 1, and the reaction was completed with a further 650 g (2.64 mols) of triethyleneglycol-monobutyl-monoallyl ether at 75° C. 1.205 g of 3-butyltriglycoloxypropyl-triethylethoxysilane (98% yield, based on the silane, and about 88% based on the glycolether) were isolated.

B.p. 170° C. (1 mbar);
$D_4^{20}$ 0.974 g;
$n_D^{20}$ 1.4334;
Viscosity (20° C.) 6.41 mPa.s.

Tris-methyltriglycol ester, produced from the triethylester in the same way as in Example 2.
$D_4^{20}$ 1.067;
$n_D^{20}$ 1.4532;
Viscosity (20° C.) 30.9 mPa.s.

EXAMPLES A) AND B)

Example 1 was repeated. The reaction started at 110° C. Without regulating the temperature, an internal temperature of 159° C. resulted. Only 50% of the trimethoxysilane (A) reacted. After dropping the temperature to 112° C., no further hydrogensilane reacted, not even after addition of more catalyst (yield 38%). Large amounts of the allyl ether were converted into the propenylether.

Triethoxysilane (B) behaved in the same way; only a 60% yield was obtained.

EXAMPLE 16

Example 1A was repeated, except that 1% by weight or 1.5% by weight of Pt-acetylacetonate, Pd-acetate, Rh-acetylacetonate and Ni-acetate were used as the catalyst. The same results were While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preparing an organosilicon compound of the formula

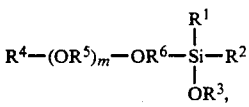

wherein
$R^1$ and $R^2$ are each independently straight or branched alkyl of 1 to 4 carbon atoms or $-OR^3$,
$R^3$ is $R^4-(OR^5)_m-$,
$R^4$ is straight or branched alkyl of 1 to 4 carbon atoms,
m is an integer from 0 to 6, inclusive,
$R^5$ is straight or branched alkylene of 2 to 4 carbon atoms, which may be identical or different when m is an integer from 2 to 6, and
$R^6$ is straight or branched alkylene of 2 to 6 carbon atoms, which comprises subjecting a hydrogensilane of the formula

wherein
$R^7$ are identical or different groups $R^4$ or the group $OR^4$,
and $R^4$ has the previously indicated meaning, to an addition reaction with a terminally unsaturated ether of the formula

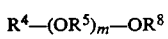

wherein
m, $R^4$ and $R^5$ have the previously indiated meanings, and
$R^8$ is terminally unsaturated straight or branched alkenyl of 2 to 6 carbon atoms, in the presence of a catalyst at a controlled temperature to form an addition product of the formula

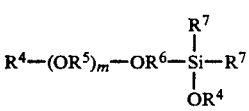

wherein
m and $R^4$, $R^5$, $R^6$ and $R^7$ have the previously indicated meanings, and the $R^4$'s are identical or different, and converting said addition product by thermal or catalytic transesterification with a monofunctional hydroxy compound of the formula

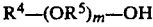

wherein
m, $R^4$ and $R^5$ have the previously indicated meanings, into said organosilicon compound.

2. The method of claim 1, wherein the catalyst in the addition reaction is a compound of an element of the eighth sub-group of the periodic system.

3. The method of claim 2, wherein said element of the eighth sub-group of the Periodic System is nickel, ruthenium, rhodium, palladium or platinum.

4. The method of claim 1, wherein the temperature of the addition reaction is controlled to stay within the range of 25° to 130° C.

5. The method of claim 1, wherein the addition reaction temperature is controlled by adding a solvent or the addition product itself, or an excess of the hydrogensilane or the terminally unsaturated ether.

6. The method of claim 1, wherein the monofunctional hydroxy compound is used in an amount equivalent to the number of $-OR^4$ groups in the addition product or in excess of 2 to 3 equivalents.

7. The method of claim 1, wherein the thermal transesterification is performed at a temperature between 90° to 240° C.

8. The method of claim 1, wherein soluble halogen-free titanium or zirconium esters are used as transesterification catalysts.

* * * * *